United States Patent [19]

Diaz et al.

[11] Patent Number: 4,820,849

[45] Date of Patent: Apr. 11, 1989

[54] PROCESS FOR REDUCING CORROSIVE IMPURITIES IN SULFOLANE USED FOR EXTRACTING AROMATIC HYDROCARBONS

[75] Inventors: Zaida Diaz, Houston; James H. Miller, Katy, both of Tex.

[73] Assignee: Shell Oil Company, Houston, Tex.

[21] Appl. No.: 139,494

[22] Filed: Dec. 30, 1987

[51] Int. Cl.$^4$ ........................................... C07D 333/48
[52] U.S. Cl. .................................................... 549/87
[58] Field of Search .......................................... 549/87

[56] References Cited

U.S. PATENT DOCUMENTS 3,252,997  5/1966  Ridderikhoff et al. ............... 549/87
4,501,902  2/1985  Cleary ................................... 549/87

FOREIGN PATENT DOCUMENTS 2163741  3/1986  United Kingdom .................. 549/87

OTHER PUBLICATIONS

Thompson Chem. Abst. 77:90966m (1972).
Thompson Chem. Abst. 76:27003j (1972).

Primary Examiner—Alan Siegel
Attorney, Agent, or Firm—Ronald R. Reper

[57] ABSTRACT

A process is disclosed for reducing the level of corrosive impurities in sulfolane solution originating from a process for the extraction of aromatic hydrocarbons from petroleum and having a pH of at least 8.5, comprises combining a sulfolane-soluble polyprotic acidic substance with said sulfolane to form a solid phase containing at least a portion of said corrosive impurities, and separating the sulfolane from the solid phase.

7 Claims, No Drawings

PROCESS FOR REDUCING CORROSIVE IMPURITIES IN SULFOLANE USED FOR EXTRACTING AROMATIC HYDROCARBONS

BACKGROUND OF THE INVENTION

The present invention relates to a process for reducing the level of corrosive impurities in sulfolane which has been used to extract aromatic hydrocarbons from petroleum. Sulfolane (tetrahydrothiophene 1,1-dioxide; also referred to as tetramethylene sulfone), is a highly polar compound having excellent solvent properties, very good chemical and thermal stability and is generally considered to be non-corrosive to carbon steel. In pure form it is colorless, but commercially available sulfolane may exhibit a dark or amber color.

Sulfolane is applied in a number of liquid-liquid and liquid-vapor extractions, and is particularly suitable for the extraction of aromatic compounds such as benzene, toluene and o,m & p-xylenes from hydrocarbon streams having a carbon number from about C6 to about C10. These aromatic compounds typically are not plentiful in crude petroleum, but are produced by thermal or catalytic reforming. Many catalytic reforming processes use a platinum-containing heterogeneous catalyst, and up to 1% of a halogen may be used as a promoter to regulate the acidity at the cracking and isomerization sites of the support, which typically is alumina granules. During catalytic reforming a number of chemical conversions occur, e.g., paraffins may be cracked and hydrogenated, or isomerized, or undergo dehydrocyclization; naphthenes with side chains may undergo dehydrocyclization, and naphthene rings are dehydrogenated into aromatic rings. Thus by selecting feed fractions that are rich in naphthenes it is possible to produce a reformate that contains 35–60% of benzenes, toluene and the xylenes. These aromatic compounds may also be extracted from, e.g., hydrotreated pyrolysis naphtha feeds.

In the course of the extraction process, impurities find their way into the sulfolane solvent, possibly from other processing steps upstream of the extraction process, and possibly from decomposition of the sulfolane. The decomposition may have been thermal or catalyzed by the various chemicals present or added to the upstream processes. These impurities can cumulate and concentrate in the sulfolane and lead to significant corrosion rates of the processing equipment used in the extraction process, and if not remedied, result in serious operating and safety problems. The use of pH control, i.e., maintaining the pH value of the sulfolane above about 8.5 by the addition of basic materials and/or corrosion inhibitors such as amines, particularly alkanolamines such as monoethanol amine, has met with but limited success in alleviating this serious problem.

A procedure has now been found which substantially reduces the level of corrosive impurities in the sulfolane at low cost and without requiring substantial amounts of costly process equipment.

SUMMARY OF THE INVENTION

In accordance with the invention there is provided a process for reducing the level of corrosive impurities in sulfolane solution originating from a process for the extraction of aromatic hydrocarbons from petroleum, which solution contains corrosive impurities and has a pH value of at least 8.5, which process comprises in sequence:

(a) adding a sulfolane-soluble polyprotic acidic substance to said sulfolane solution to form a solid phase containing at least a portion of said corrosive impurities and a liquid phase having reduced corrosive/impurity content, and (b) separating said liquid phase from step (a) from said solid phase.

In a preferred embodiment, the separated liquid phase is contacted with particulate alumina to further remove corrosive impurities.

DESCRIPTION OF THE PREFERRED EMBODIMENTS

The sulfolane solvent suitably employed as feed in the present process includes sulfolane containing corrosive materials such as chlorides, sulfates, sulfolane degradation products such as carboxylic and sulphonic acids, and also containing reaction products of such materials with materials conventionally added to mitigate their corrosive effect, such as amines, particularly alkanolamines. Conventionally sulfolane solvent employed in aromatics extraction will contain a small amount of water, e.g., from about 0.5 to about 3 per cent by weight. The sulfolane starting material may be highly colored and will ordinarily have a pH above about 8.3, particularly above about 8.5.

According to the invention a polyprotic acidic substance is slowly combined with the corrosives-containing sulfolane liquid to form a solid phase, i.e., a precipitate, from which the remaining liquid phase is separated. The separated sulfolane liquid is found to exhibit substantially reduced corrosivity as measured by conventional corrosion rate tests on metal coupons.

The acidic substance employed is a polyprotic acidic material such as sulfuric acid or phosphoric acid, used in either concentrated or dilute form; attempts to reduce the corrosive nature of the sulfolane by addition of monoprotic acids such as concentrated hydrochloric or nitric acid, or contact with a strong ion exchange resin to lower the pH of the sulfolane solution have not been successful in forming a solid phase and/or removing the corrosives to a material degree.

Generally the polyprotic acidic substance employed may be diprotic, triprotic, or if preferred, in the form of an anhydride of a polyprotic acid, such as carbon dioxide or phosphorus trioxide. Owing to the corrosive nature of many halogen compounds it is preferred that a non-halogen containing acidic substance be used. Particularly preferred are phosphorus-containing acids. Exemplary are phosphoric acid, hypophosphorous acid, phosphorous acid, pyrophosphoric acid and hypophosphoric acid. It is also possible to employ sulfolane soluble acidic salts of these acids. Particularly preferred, owing to their ready availability and relatively lower cost are carbon dioxide and orthophosphoric acid.

The acidic substance may be combined with the liquid sulfolane solution by any known method, but preferably is slowly mixed in with slow stirring of the mixture. The mixing may take place at any convenient temperature, e.g., from about 20 to about 100 degrees C.; good results have been obtained at ambient temperature, i.e., about 25 degrees C. Generally it is preferred to lower the pH of the corrosives-containing pH to a value in the range from about 5 to about 8, particularly from about 5.5 to 7.5. However, if the original pH value of the sulfolane is above about 9, and there are substantial amounts of impurities present, a solid phase and concurrent reduction in corrosivity of the sulfolane have been obtained by lowering the pH to a value as high as 8.6.

The solid phase may be separated by any conventional method such as, for example, decantation, filtration, centrifugation, aspiration of the liquid from above the settled solids, and the like. Typically the solids are gelatinous or tarry in nature, and may be highly colored, i.e., may be darkish brown to black.

In a preferred embodiment the sulfolane solution after separation from the solid phase is contacted with particulate alumina to further reduce the level of corrosive impurities. It has been found that contacting of the sulfolane solution feed with alumina, without having first undergone the treatment with a polyprotic acidic substance may rapidly exhaust the alumina. However, after such acidic pretreatment contacting of the sulfolane with particulate alumina may be of great benefit in further reducing the corrosive impurities, particularly when they were originally present in high concentration.

The further contacting of the sulfolane liquid phase with the particulate alumina may employ any known liquid-solid contacting procedure; passing said liquid through a bed of alumina particles has been found to be both convenient and effective. The alumina has been found effective in further reducing the corrosive nature of up to about 15 bed volumes of sulfolane liquid separated from the solid phase after treatment with the acid-acting substance.

The invention will now be illustrated with reference to the following examples.

EXAMPLE I

A sample of sulfolane solvent which had been used in service for extracting benzene from a petroleum stream and containing triethanolamine inhibitor was found to have a pH of 9.0, a chloride ion content of about 1045 parts per million by weight (ppmw), a total nitrogen content of about 0.63 per cent by weight (%w) and when measured by immersion of a carbon steel coupon in the sulfolane liquid at 400 degrees F. for about 24 hours was found to exhibit a calculated corrosion rate of 74 mils/year. This sulfolane was combined with orthophosphoric acid (85% $H_3PO_4$) to lower the pH of the combined material to about 7.0. About 1.5 grams of acid per 100 grams of sulfolane was required, and resulted in formation of a dark tarry solid phase. The liquid was separated by vacuum filtration through a #541 Whatman filter paper. The separated liquid was found to have a chloride content of about 400 ppmw, a total nitrogen content of 0.27% W and to exhibit a carbon steel corrosion rate of about 2 mils/year.

EXAMPLE II

For comparison purposes the sulfolane of example I was combined with a highly acidic ion exchange resin available under the tradename Dowex MSC-1 (H+form) at the rate of 8 grams of resin per 100 grams of sulfolane to lower the pH of the sulfolane to about 7.2. No solid phase formed; the resulting sulfolane liquid exhibited a carbon steel corrosion rate of 78 mils/year.

EXAMPLE III

A different sample of sulfolane used for extracting benzene, toluene and xylene from a catalytically reformed petroleum stream and containing diethanolamine inhibitor was found to have a pH of 10.0, a chloride content of 335 ppmw, and to exhibit a carbon steel corrosion rate of 16 mils/year. This sulfolane was contacted with a bed of particulate alumina available under the tradename Alcoa F-1 and found that breakthrough of the chloride ion at a content of about 150 ppmw was experienced after only 7 bed volumes of the sulfolane had passed through the bed of alumina. A portion of the uncontacted sulfolane was combined by slow stirring with concentrated (85% $H_3PO_4$) phosphoric acid, and at a pH of 8.6 a solid phase formed. The liquid phase was separated as in Example I and found to have a carbon steel corrosion rate of about 3 mils/year. Another portion of this uncontacted sulfolane was combined with concentrated phosphoric acid to lower the pH of the resulting liquid to 7.0. The separated liquid phase was found to have a corrosion rate of about 2 mils/year.

EXAMPLE IV

A sample of sulfolane similar to that of example I and exhibiting an average carbon steel corrosion rate of about 57 mils/year was placed in a pressure vessel which was then pressured with carbon dioxide to a pressure of 600 p.s.i.g. and allowed to equilibrate while the liquid was magnetically stirred. After 22 hours the vessel was depressured and the sulfolane examined. A solid phase had formed. The separated sulfolane liquid had a pH of 7.7 and exhibited a carbon steel corrosion rate of about 5 mils/year.

EXAMPLE V

The sulfolane of Example IV was combined with concentrated sulfuric acid to a pH of 7.0 resulting in formation of a solid phase. The separated sulfolane liquid was found to exhibit a carbon steel corrosion rate of 23 mils/year.

EXAMPLE VI

For purposes of comparison acidic substances not according to the invention were combined with sulfolane. The procedure of example V was repeated except that nitric acid was employed. No solid phase formed and the resulting liquid exhibited a carbon steel corrosion rate of 71 mils/year. The procedure was again repeated except that hydrochloric acid was employed and the pH was lowered to a value of 7.2. No solid phase formed. The resulting liquid was found to exhibit a carbon steel corrosion rate of 227 mils/year.

What is claimed:

1. A process for reducing the level of corrosive impurities in sulfolane solution originating from a process for the extraction of aromatic hydrocarbons from petroleum, which solution contains corrosive impurities and has pH value of at least 8.5, which process comprises in sequence:
   (a) adding a sulfolane-soluble polyprotic acidic substance or an anhydride of a polyprotic acid to said sulfolane solution to form a solid phase containing at least a portion of said corrosive impurities and a liquid phase having reduced corrosive impurity content, and
   (b) separating said liquid phase from step (a) from said solid phase.

2. A process as in claim 1 wherein said polyprotic acidic substance or an anhydride of a polyprotic acid is added in an amount sufficient to lower the pH of the sulfolane of a pH value in the range from about 5 to 8, inclusive.

3. A process as in claim 2 wherein the pH value is lowered by the addition of a non-halogen containing polyprotic acidic substance to said sulfolane solution.

4. A process as in claim 1 wherein said polyprotic acidic substance is a phosphorus-containing acid.

5. A process as in claim 1 wherein said polyprotic acidic substance or an anhydride of a polyprotic acid is selected from the group of carbon dioxide and orthophosphoric acid.

6. A process as in claim 5 wherein the separated liquid phase from step (b) is contacted with particulate alumina.

7. A process as in claim 6 wherein said contacting takes place by passing up to about 15 bed volumes of sulfolane through a bed of alumina.

* * * * *